United States Patent [19]

Vincent et al.

[11] Patent Number: 4,935,525

[45] Date of Patent: Jun. 19, 1990

[54] PROCESS FOR THE INDUSTRIAL SYNTHESIS OF (2S, 3AS, 7AS) 2-CARBOXY PERHYDROINDOLE, APPLICATION TO THE INDUSTRIAL SYNTHESIS OF CARBOXYALKYL DIPEPTIDES

[75] Inventors: Michel Vincent, Bagneux; Jean Baliarda, Anthony; Bernard Marchand, Checky; Georges Remond, Versailles, all of France

[73] Assignee: Adir et Cie, Neuilly-sur-Seine, France

[21] Appl. No.: 245,352

[22] Filed: Sep. 16, 1988

[30] Foreign Application Priority Data

Sep. 17, 1987 [FR] France .................. 87 12900

[51] Int. Cl.$^5$ ............................. C07D 209/34
[52] U.S. Cl. ................. 548/452; 548/491
[58] Field of Search .................. 548/452, 491

[56] References Cited

U.S. PATENT DOCUMENTS

4,303,583 12/1981 Kim ..................... 548/492
4,520,205 5/1985 Buzby .................. 548/491
4,659,838 4/1987 Lerch ................... 548/452

FOREIGN PATENT DOCUMENTS

0037231 10/1981 European Pat. Off. .
8303828 11/1983 World Int. Prop. O. .

*Primary Examiner*—Johnnie R. Brown
*Assistant Examiner*—Frederick F. Tsung
*Attorney, Agent, or Firm*—Gordon W. Hueschen

[57] ABSTRACT

Process for the industrial synthesis of (2S, 3 7aS)-2-carboxyperhydroindole by reduction of 2-carbox indole or of one of its esters to (R,S)-2-carboxyindo or of one of its esters which, after saponification, converted into the acid, the S isomer of (R,S)-2-carboxyindoline being obtained by precipitation from the mixture of the two (R) and (S) isomers, in the presence of (+) methylbenzylamine, (S)-2-carboxyindoline being in its turn subjected to catalytic hydrogenation to give (2S, 3aS,7aS)-2-carboxyperhydroindole, after separation of (2S,3aR,-7aR) isomer by crystallization.

Application to the synthesis of carboxyalkyl d peptides capable of being employed in therapeutics.

7 Claims, No Drawings

PROCESS FOR THE INDUSTRIAL SYNTHESIS OF (2S, 3AS, 7AS) 2-CARBOXY PERHYDROINDOLE, APPLICATION TO THE INDUSTRIAL SYNTHESIS OF CARBOXYALKYL DIPEPTIDES

The present invention relates to a new process for the industrial synthesis of (2S,3aS,7aS)2-carboxyperhydroindole and its application in the industrial synthesis of carboxylalkyl dipeptides.

More specifically, the present invention relates to a process for the industrial synthesis of 2-carboxyperhydroindole and its application to the synthesis of carboxyalkyl dipeptides of formula (I):

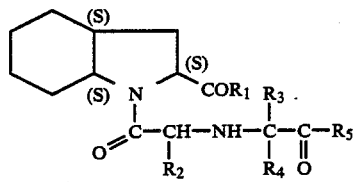

and their pharmaceutically acceptable salts, in which formula:

$R_1$ and $R_5$, which are identical or different, are hydroxy, lower alkoxy, lower alkenyloxy, lower dialkylamino-lower alkoxy, acylamino-lower alkoxy, acyloxy-lower alkoxy, aryloxy, aryl-lower alkoxy, amino, lower alkylamino, lower dialkylamino, hydroxyamino, aryl-lower alkylamino or substituted aryloxy or substituted aryl-lower alkoxy, where the substituent is methyl, halo or methoxy;

$R_2$ is hydrogen, lower alkyl, aryl-lower alkyl, aminomethylphenyl-lower alkyl, hydroxyphenyl-lower alkyl, hydroxy-lower alkyl, acylamino-lower alkyl, amino-lower alkyl, dimethylamino-lower alkyl, guanidino-lower alkyl, imidazolyl-lower-alkyl, indolyl-lower alkyl or lower alkylthio-lower alkyl;

$R_3$ is hydrogen, a linear or branched alkyl with 1 to 10 carbon atoms, a lower alkyl substituted by one or more substituents chosen from halo, hydroxy, lower alkoxy, aryloxy, substituted aryloxy, heteroaryloxy, substituted heteroaryloxy, amino, lower alkylamino, lower dialkylamino, acylamino, arylamino, substituted arylamino, guanidino, imidazolyl, indolyl, lower alkylthio, arylthio, substituted arylthio, carboxy, carbamoyl, lower alkoxy-carbonyl, or else $R_3$ is aryl, substituted aryl, lower aralkyl, lower aralkenyl, substituted lower aralkyl, substituted lower aralkenyl, lower heteroaralkyl, substituted lower heteroaralkyl, lower heteroaralkenyl, substituted lower heteroaralkenyl, aralkyloxy, substituted aralkyloxy, heteroaralkyloxy, substituted heteroaralkyloxy, aralkylthio, substituted aralkylthio, heteroaralkylthio or substituted heteroaralkylthio, the aryl or heteroaryl moiety of the abovementioned substituted aryloxy, heteroaryloxy, arylamino, arylthio, aryl, aralkyloxy, heteroaralkyloxy, aralkylthio, heteroaralkylthio, lower aralkyl, lower aralkenyl, lower heteroaralkenyl or lower heteroaralkyl being substituted by one or more groups chosen from halo, lower alkyl, hydroxy, lower alkoxy, amino, acylamino, lower alkylamino, lower dialkylamino, carboxyl, cyano or sulfamoyl; the alkyl moiety of the abovementioned substituted aralkyloxy, aralkylthio, lower aralkyl, lower heteroaralkyl, heteroaralkyloxy or heteroaralkylthio being substituted by one or more groups also chosen from halo, lower alkyl, hydroxy, lower alkoxy, amino, acylamino, lower alkylamino, lower dialkylamino, carboxyl, cyano or sulfamoyl;

$R_4$ is hydrogen or a lower alkyl group.

It should be stated that, among the abovementioned values, the term "acyl" includes the radicals

in which $R_6$ denotes lower alkyl, lower alkenyl or aryl.

The terms lower alkyl and lower alkenyl also denote any hydrocarbon radical with 1 to 6 carbon atoms, be they linear or branched, such as methyl, ethyl, n-propyl, isopropyl n-butyl, isobutyl, sec-butyl, tert-butyl, pentyl, vinyl, allyl, and the like.

The term aryl means, unless stated otherwise, phenyl or naphthyl, optionally substituted by one or more lower alkyl or alkyloxy groups, such as toluyl, xylyl, and the like.

The term heteroaryl may be illustrated by pyridyl, thienyl, furyl, pyrrolyl, benzothienyl, benzofuryl, indolyl, thiazolyl, imidazolyl, oxazolyl, benzimidazolyl, benziothiazolyl or benzoxazolyl radicals, as well as by one of the preceding resulting from the substitution of one or more —CH— chain units by an —N— chain unit.

Among the compounds of formula (I), the preferred ones are those in which:

$R_1$ and $R_5$ are, independently of each other, a hydroxy or linear or branched lower alkoxy group, $R_2$ is a linear or branched lower alkyl group optionally substituted by an amino group, $R_3$ is a linear or branched lower alkyl group optionally substituted by a cycloalkyl or aryl radical such as phenyl, and among these, the n-propyl, n-butyl and phenylethyl groups are preferred, $R_4$ is a hydrogen atom.

The preferred compound of formula (I) is perindopril of formula (II):

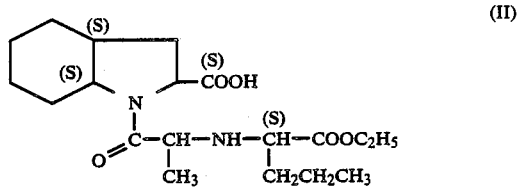

or (2S,3aS,7aS)-1-{2-[1-(ethoxycarbonyl)-(S)-butylamino]-(S)-propionyl}octahydroindole-2-carboxylic acid, as well as its addition salts with a pharmaceutically acceptable acid or base, in the case of which the process of the present invention may be applied more particularly.

The compounds of formula (I) as well as their salts have interesting pharmacological properties. In particular, they exert an inhibiting activity on certain enzymes, such as carboxypolypeptidases, enkephalinases or kininase II. In particular, they inhibit the conversion of the angiotensin I decapeptide to angiotensin II octapeptide, responsible in certain cases for arterial hypertension, by acting on the conversion enzyme.

The use of these compounds in therapeutics makes it possible, therefore, to reduce or even to suppress the activity of these enzymes, which are responsible for the hypertensive disorder or for cardiac insufficiency. The action on kininase II results in an increase in the circulating bradykinin and also in a lowering of the arterial pressure via this route.

Compounds of formula (I), their preparation, and their use in therapeutics have been described in European Patent Nos. 0,049,658, 0,088,341 and in European Patent Applications Nos. 0,154,886 and 0,046,953. The derivative of formula (II), its preparation and its use in therapeutics have been described in European Patent No. 0,049,658.

In particular, one of the starting materials which can be employed for the preparation of the compounds of formula (I) is 2-carboxyperhydroindole, described in European Patent Application No. 0,037,231, as well as its esters of formula (III):

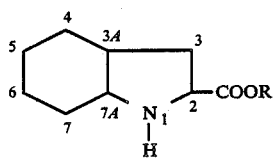

(III)

where R denotes a lower alkyl or benzyl group, or a hydrogen atom.

The compounds of formula (III) exist in the form of four racemic pairs:
the two cis IIIa and IIIb epimers,
the two trans IIIc and IIId epimers,

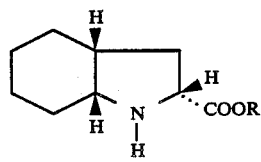

(±) IIIa
cis, endo
2S, 3aS, 7aS ou 2R, 3aR, 7aR

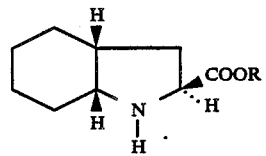

(±) IIIb
cis, exo
2S, 3aR, 7aR ou 2R, 3aS, 7aS

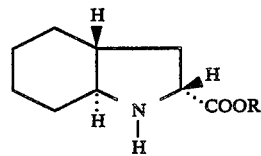

(±) IIIc
trans α
2S, 3aS, 7aR ou 2R, 3aR, 7aS

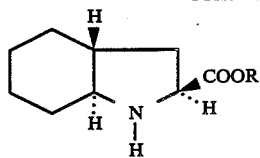

(±) IIId
trans β
2R, 3aS, 7aR ou 2S, 3aR, 7aS

The preparation of these compounds of formula (III) may be carried out by means of well-known methods of the prior art (EP 0,037,231, EP 0,084,164, EP 0,115,345, EP 0,173,199, EP 0,132,580).

However, the isomer employed specifically in the synthesis of the compounds of formula (I) is (2S,3aS,-7aS)-2-carboxyperhydroindole, as well as its esters of formula (IIIaS):

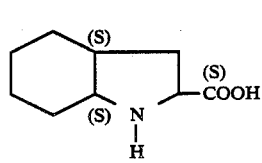

(IIIaS)

It is known, in fact (EP 37,231, EP 49,658, EP 88,341 and EP 154,886), that the compounds of formula (I) in which the configuration of the bicyclic system is 2S,3aS,7aS have an activity which is markedly higher than that of the compounds in the case of which the cis configuration of the bicyclic system is different.

The preparation of (2S,3aS,7aS)-2-carboxyperhydroindole may be carried out according to the methods described in the prior art (EP 0,037,231, EP 0,115,345, EP 0,173,199, EP 0,132,580).

Some of these employ 2-carboxyindole as starting material, which has the advantage of being a starting material which is readily available and relatively inexpensive (EP 0,037,231), and which is subjected to catalytic reduction on rhodized charcoal to give a mixture of both cis endo isomers of 2S,3aS,7aS and 2R,3aR,7aR configuration respectively.

However, the separation of the 2S,3aS,7aS isomer, which is used in the synthesis of the carboxyalkyl dipeptides of formula (I), from the 2R,3aR,7aR isomer generally requires the use of methods which are particularly arduous to employ.

Thus, to perform this separation of the 2S,3aS, 7aS, and 2R,3aR,7aR (cis, endo racemic) isomers, U.S. Pat. No. 0,037,231 employs many stages requiring the synthesis of the N-benzoyl compound, fractional crystallization of the salt of the diastereoisomer with S-α-phenylethylamine, the liberation of the two N-benzoyl SSS and RRR derivatives, and then the removal of the benzoyl group, followed by a pass through an ion exchange column and a recrystallization.

For this same separation, European Patent Application No. 0,115,345 employs several stages requiring the esterification of the carboxylic acid group with benzyl alcohol, conversion of the amino ester into a salt with (S)-N-benzyloxycarbonylphenylalanine, separation of the S,S,S isomer by fractional crystallization, and the liberation of the amino group, optionally followed by the liberation of the carboxylic acid group.

The Applicant Company has now found an original process for the synthesis of (2S,3aS,7aS)-2-carboxyperhydroindole, which also offers the advantage of employing 2-carboxyindole as starting material, but which does not offer the disadvantage of this arduous separation of the two 2S,3aS,7aS and 2R,3aR,7aR isomers of carboxyperhydroindole, since, in a first step, the carboxyindole is reduced to carboxyindoline to give a mixture of (2R) and (2S)-2-carboxyindolines which are easily separated in a single stage by fractional crystallization; the (2S) isomer being then subjected to catalytic hydrogenation, to lead stereoselectively to (2S,3aS,7aS)-2-carboxyperhydroindole, after crystallization from a strictly chosen polar solvent.

More particularly, the synthesis of (2S,3aS,7aS,)-2-carboxyperhydroindole, which has now been found by the Applicant Company, employs as starting material 2-carboxyindole or one of its esters of formula (IV):

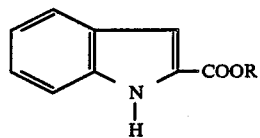

(IV)

in which R denotes a lower alkyl or benzyl group or a hydrogen atom,
which is subjected to reduction by a process such as the use of the tin/hydrochloric acid couple at ambient temperature in a lower aliphatic alcohol medium, to (R,S)-2-indoline acid or to one of its esters of formula (V):

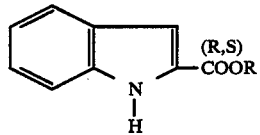

(V)

in which R has the same meaning as in formula (IV), which, when R=H, is the (R,S)-2-carboxyindoline of formula (VI);
which, when R is other than H, is converted by alkaline hydrolysis into (R,S)-2-carboxyindoline of formula (VI):

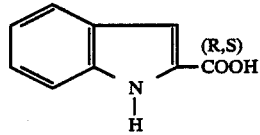

(VI)

consisting, in fact, of a mixture of two isomers according to whether the carbon bearing the carboxyl is:
in the R configuration (R isomer),
in the S configuration (S isomer),
from which mixture the S isomer is isolated by adding the said mixture to a solution of (+)-α-methylbenzylamine in a lower aliphatic alcohol, to obtain a precipitate of the salt of (S)-2-carboxyindoline with α-methylbenzylamine, which, after filtration, is dissolved in water, the solution obtained being then acidified to permit the liberation of (S)-2-carboxyindoline, which is subjected to catalytic hydrogenation, the catalyst being chosen from platinum, nickel, palladium or rhodium, mixed with a support such as charcoal, so as to make it possible to obtain a maximum proportion of (2S,3aS,7aS)-2-carboxyperhydroindole, the latter being separated from the (2S,3aR,7aR) isomer obtained in a low proportion by a single crystallization, by means of a solvent strictly selected from lower aliphatic alcohol, acetonitrile, dioxane and ethyl acetate, by itself or mixed with each other or mixed with water, provided that the mixture forms a single phase.

It should be noted that (R)-2-carboxyindoline can be separated from (R,S)-2-carboxyindoline by employing the same procedure as in the case of (S)-2-indoline acid; it then suffices to employ (−)-α-methylbenzylamine.

The invention also extends to the original products obtained while this process is performed and, more particularly, to the salts formed by α-methylbenzylamine with the isomers of 2-carboxyindoline, and more particularly with (S)-2-carboxyindoline.

The following example illustrates the invention, but does not limit it in any way.

EXAMPLE:
(2S,3aS,7aS)-2-CARBOXYOCTAHYDROINDOLE

Stage A

2-Ethoxycarbonylindole

Heat 5 kg of 2-carboxyindole suspended in ethanol in the presence of sulfuric acid to boiling for 8 hours. Evaporate off the ethanol, then take up with 40 liters of ethyl acetate and wash the organic solution with an aqueous sodium hydroxide solution and dry.

Evaporate off the ethyl acetate, take up the crystalline mass with hexane. After filtering off and drying, 5.3 kg of crystals are obtained.

Melting point: 123°–125° C.

Microanalysis: Calculated: C % 69.83, H % 5.86, N % 7.40. Found: C % 69.56, H % 5.74, N % 7.30.

Spectrometry in the infrared: 2150 cm$^{-1}$ (NH), 1680 cm$^{-12}$ (carboxylic acid).

Stage B (R,S)-2-Ethoxycarbonyl indoline

Suspend 10 kg of 2-ethoxycarbonylindoline obtained earlier in 110 liters of hydrochloric ethanol in a reactor. Next, add 20 kg of granulated tin. Keep stirring for approximately 2 days at ambient temperature.

Evaporate off the ethanol, take up the residue with water and add 110 liters of toluene. Stir for approximately 20 minutes. Alkalify with aqueous ammonia. Separate off the aqueous phase and extract it once again with 150 liters of toluene.

Combine the toluene phases and wash them with water. Separate off the toluene phases, filter.

Remove the water by distilling the water-toluene azeotrope. Cool and pass through a stream of anhydrous HCl gas.

Cool. Evaporate and wash with pure toluene.

Weight obtained: 10.11 kg.

Yield: 84%.

Thin layer chromatography: Solvent: toluene: 10, ethyl acetate: 5. Support: Merck silica 60 F 254. Developer: UV. $R_f$: 0.55.

Stage C

(R,S)-2-Carboxyindoline 2.15 kg of (R,S)-2-ethoxycarbonylindoline dissolved in ethanol are saponified with 12.5 liters of N sodium hydroxide, with stirring for 24 hours. After washing the alkaline solution, neutralize with concentrated hydrochloric acid. After filtering off, washing and drying, 1.57 kg of white crystals of the expected product are obtained.

Yield: 86%.
Melting point: 188°–189° C.
Spectrometry in the infrared: $NH_2{}^+$: 2500–2000 $cm^{-1}$. $COO^-$: 1620 $cm^{-1}$.

Stage D

(S)-2-Carboxyindoline 6.05 kg of (R,S)-2-carboxyindoline are added to a solution of 4.49 kg of (+)-α-methylbenzylamine in anhydrous ethanol. A white precipitated product is obtained which, after filtering off, is digested in refluxing isopropanol. After cooling, the solid is filtered off and washed with a little isopropanol; the white crystals obtained are dried: 3.68 kg.

Rotatory power:

$$|\alpha|_{21}{}^D = -5.3 \; (c=1\% \text{ ethanol})$$

(S)-2-Carboxyindoline is prepared in a quantitative yield by dissolving 1 kg of the above salt in 5 liters of water and neutralizing with an aqueous hydrochloric acid solution. This precipitate is filtered off, washed with water and dried.

Stage E

(2S,3aS,7aS)-2-Carboxyoctahydroindole

Place 25 kg of (S)-2-carboxyindoline obtained previously in 110 liters of methanol in a vessel. Keep stirred. Charge the rhodium catalyst (5% dry) into a mixer.

In a hydrogenator, start up the stirring, and charge the methanolic suspension of (S)-2-carboxyindoline by making it flow through the mixer and rinse the assembly with water. Heat to 60° C. and pressurize with hydrogen.

Filter off the catalyst on a single-plate filter. Collect the hydroalcoholic liquors in a reactor and evaporate off the methanol under vacuum.

After concentrating, charge approximately 300 kg of dioxane. Heat to boiling and add water until a solution is obtained. Allow to cool. Filter off and dry.

22.3 kg of crystals are obtained.
Yield: 86.1%.

We claim:

1. A process for the industrial preparation of (2S,3aS,7aS)-2-carboxyperhydroindole of formula (IIIaS):

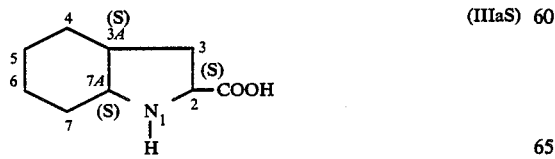

wherein the starting material employed is 2-carboxyindole or one of its esters of formula (IV):

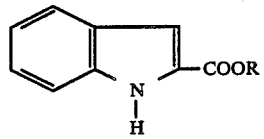

optionally converted into a salt with an acid AH, in which formula R denotes a hydrogen atom or a lower alkyl group,
which is subjected to reduction by a process such as the use of the tin-hydrochloric acid couple, to lead to (R,S)-2-carboxyindoline or to one of its esters of formula (V):

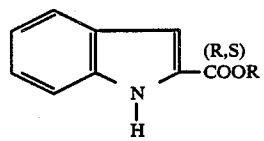

in which R has the same meaning as in the formula (IV), which, when R=H, is the (R,S)-2-carboxyindoline of formula (VI);
which, when R is other than H, is converted by alkaline hydrolysis into (R,S)-2-carboxyindoline of formula (VI):

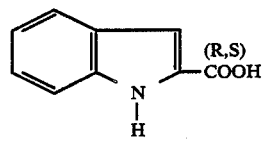

consisting, in fact, of a mixture of two isomers according to whether the carbon bearing the carboxyl is:
in the R configuration (R isomer),
in the S configuration (S isomer),
from which mixture the S isomer is isolated by adding the said mixture to a solution of (+)-α-methylbenzylamine in a lower aliphatic alcohol, to obtain,
a precipitate of the salt of (S)-2-carboxyindoline with (+)-α-methylbenzylamine,
which, after filtration, is dissolved in water, the solution obtained being then acidified to permit the liberation of (S)-2-carboxyindoline,
which is subjected to catalytic hydrogenation, the catalyst being chosen from nickel, platinum, palladium or rhodium, mixed with a support such as charcoal, so as to make it possible to obtain a maximum proportion of (2S,3aS,7aS)-2-carboxyperhydroindole, the latter being separated from the (2S,3aR,7aR) isomer obtained in a low proportion by a single crystallization in a polar solvent carefully chosen from lower aliphatic alcohol, acetonitrile, dioxane or ethyl acetate, by itself or mixed with each other or mixed with water, provided that the mixture forms a single phase.

2. A process for the industrial synthesis of (2S, 3aS,7aS)-2-carboxyperhydroindole as claimed in claim 1, wherein the starting material employed is the ethyl ester of 2-carboxyindole of formula (IVo):

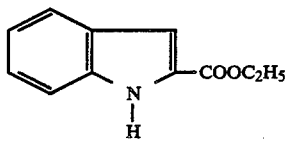

itself obtained by esterification of 2-carboxyindole with ethanol in the presence of an esterification catalyst such as sulfuric acid.

3. A process as claimed in claim 1, wherein the precipitation of (S)-2-carboxyindoline with (+)-α-methylbenzylamine is performed in ethanol.

4. A process as claimed in claim 1, wherein the reduction of the carboxyindole or of one of its esters of formula (VI), which are optionally converted into a salt, to (R,S)-2-carboxyindoline is performed by means of the tin-hydrochloric acid couple in a lower aliphatic alcohol medium, and at ambient temperature.

5. A process as claimed in claim 1, wherein the reduction of (S)-2-carboxyindoline to 2-carboxyperhydroindole is performed using rhodium on charcoal as catalyst.

6. A process as claimed in claim 1, wherein the recrystallization for the purpose of isolating the (2S,3aS,7aS)-2-carboxyperhydroindole from the reaction mixture obtained after catalytic reduction of (S)-2-carboxyindoline is performed using a dioxane-water mixture as a solvent.

7. A process as claimed in claim 1, wherein the crystallization of the salt of (S)-2-carboxyindoline with (+)-α-methylbenzylamine is carried out in isopropanol.

* * * * *

UNITED STATES PATENT AND TRADEMARK OFFICE
CERTIFICATE OF CORRECTION

PATENT NO. : 4,935,525

DATED : June 19, 1990

INVENTOR(S) : Michel Vincent, Jean Baliarda, Bernard Marchand, Georges Remond Page 1 of 2

It is certified that error appears in the above-identified patent and that said Letters Patent is hereby corrected as shown below:

Title Page, [75] Inventors: Bernard Marchand, "Checky" should read -- Checy --.

Title Page [56] References Cited, U. S. PATENT DOCUMENTS, 4,520,205 5/1985 "Buzby" should read -- Buzby, Jr. --.

Column 1, line 8; "7aS)2-" should read -- 7aS)-2- --.

Signed and Sealed this

Eleventh Day of June, 1991

Attest:

*Attesting Officer*

HARRY F. MANBECK, JR.

*Commissioner of Patents and Trademarks*

UNITED STATES PATENT AND TRADEMARK OFFICE
CERTIFICATE OF CORRECTION

PATENT NO.  : 4,935,525

DATED       : June 19, 1990

INVENTOR(S) : Michel Vincent, Jean Baliarda, Bernard Marchand, Georges Remond

It is certified that error appears in the above-identified patent and that said Letters Patent is hereby corrected as shown below:

Column 2, line 47;

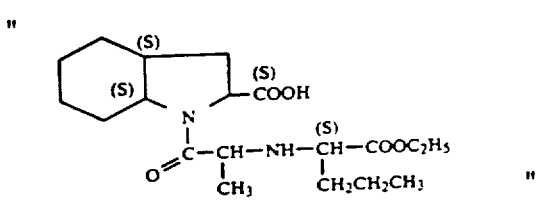 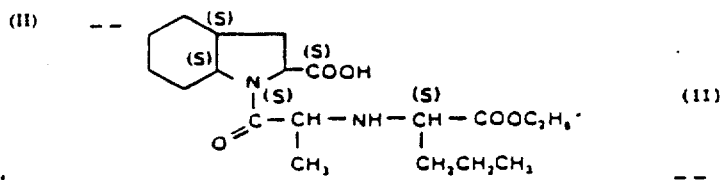

should read (See middle of formula "N" should read -- N (s) --)

Signed and Sealed this

Eleventh Day of June, 1991

Attest:

HARRY F. MANBECK, JR.

Attesting Officer

Commissioner of Patents and Trademarks

UNITED STATES PATENT AND TRADEMARK OFFICE
CERTIFICATE OF CORRECTION

PATENT NO. : 4,935,525

DATED : June 19, 1990

INVENTOR(S) : Michel Vincent, Jean Baliarda, Bernard Marchand, Georges Remond It is certified that error appears in the above-identified patent and that said Letters Patent is hereby corrected as shown below:

The following corrections are located on the Title Page [57], ABSTRACT:

Line 1; "3 7aS)" should read -- 3aS, 7aS) --.

Line 2; "2-carbox indole" should read -- 2-carboxyindole --.

Line 3; "-carboxyindo" should read -- -carboxyindoline --

Line 4; "saponification, converted" should read
  -- saponification, is converted --.

Line 5; "cf" should read -- of --.

Line 7/8; "(+) methylbenzylamine," should read
  -- (+) - α - methylbenzylamine --.

Line 10; "of (2S," should read -- of the (2S, --.

Line 12; "d peptides" should read -- dipeptides --.

Signed and Sealed this

Eleventh Day of February, 1992

Attest:

HARRY F. MANBECK, JR.

Attesting Officer

Commissioner of Patents and Trademarks